United States Patent

Suzuki et al.

(10) Patent No.: US 6,492,369 B2
(45) Date of Patent: Dec. 10, 2002

(54) THERAPEUTIC AGENTS FOR DRUG DEPENDENCE

(75) Inventors: Tsutomu Suzuki, Yokohama (JP); Shiro Mita, Nishinomiya (JP); Kiyoshi Matsuno, Toyonaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/850,431

(22) Filed: May 7, 2001

(65) Prior Publication Data

US 2002/0019399 A1 Feb. 14, 2002

Related U.S. Application Data

(63) Continuation-in-part of application No. PCT/JP99/06148, filed on Nov. 4, 1999.

(30) Foreign Application Priority Data

Nov. 9, 1998 (JP) .............................. 10-317468

(51) Int. Cl.$^7$ ........................ A61K 31/495; A61K 31/50
(52) U.S. Cl. ................ 514/252.12; 514/810; 514/811; 514/812; 514/813
(58) Field of Search ..................................... 514/252.12

(56) References Cited

U.S. PATENT DOCUMENTS 5,556,857 A  9/1996  Oshiro et al.

FOREIGN PATENT DOCUMENTS

| EP | 711763 | 5/1996 |
| JP | 7-89949 | 4/1995 |
| JP | 10-120569 | 5/1998 |
| WO | WO 93/00313 | 1/1993 |
| WO | WO 95/00131 | 1/1995 |

OTHER PUBLICATIONS

CA132:329943, Suzuki et al, WO 2000027933, May 18, 2000, abstract.*
Sahiko Tanaka and Takemi Yoshia, *Pharmacia*, (1998), 900–904, 34 Partial English language translation enclosed abstract.

Jun Ishigooka, *Pharmacia*, (1998), 905–909, 34 Partial English language translation enclosed abstract.

Tsutomu Suzuki, Tomoji Yanagita, Akira Yamamoto, Kiyoshi Wada and Tsuneyuki Yamamoto, *Pharmacia*, (1998), 877–882 Partial English language translation enclosed abstract.

*New Pharmacology*, (1989), 606–611, Nankodo Partial English language translation enclosed abstract.

*Opioid*, (1991), 118–120, Kagakudojin Partial English language translation enclosed abstract.

* cited by examiner

*Primary Examiner*—Rebecca Cook
(74) *Attorney, Agent, or Firm*—Frishauf, Holtz, Goodman & Chick, P.C.

(57) ABSTRACT

A method for preventing or treating drug dependence comprising administering to a human in need thereof a pharmaceutically effective amount of a 1,4-(diphenylalkyl) piperazine compound represented by the following formula [I] or a pharmaceutically acceptable salt thereof, wherein $R^1$ is lower alkoxy; $R^2$ is lower alkoxy; A is lower alkylene and B is lower alkylene;

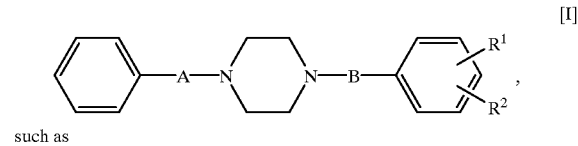

such as

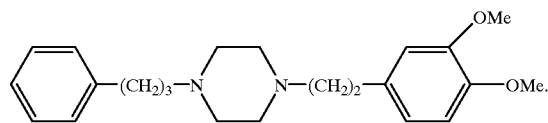

9 Claims, No Drawings

THERAPEUTIC AGENTS FOR DRUG DEPENDENCE

CROSS REFERENCE TO RELATED APPLICATION

This application is a continuation-in-part application of International Application No. PCT/JP99/06148 (not published in English), filed Nov. 4, 1999, the entire contents of which are incorporated by reference herein.

BACKGROUND OF THE INVENTION

1. Field of the Invention

The present invention relates to drugs which contain 1,4-(diphenylalkyl)piperazine derivatives as active ingredients and are useful for the prevention or treatment of drug dependence due to drug abuse.

2. Background Art

Drug dependence is a functional adaptive condition of the central nervous system changed by interactions between living bodies and drugs. Drug dependence is classified as a psychological dependence wherein one depends on the psychological effects of drugs and has a physical dependence to avoid unpleasant bioreactions due to withdrawal (withdrawal symptoms). Symptoms always observed in drug dependence are psychological dependence on drugs which have been ingested and a strong impulse to demand the drugs (Pharmacia, 34, 900–904 (1998)).

A fear of drug dependence due to drug abuse is a serious social problem. There is not yet a direct therapy of the psychological dependence, which is the essence of drug dependence, and addiction, which is its symptom (Pharmacia, 34, 905–909 (1998)). An agonist therapy of cocaine and the like are actively being studied as a pharmacotherapy of drug dependence (Pharmacia, 34, 877–882 (1998)).

All the addicting drugs act on the central nervous system as main effects or side effects and are roughly classified as opioid analgesics, central nervous system depressants, central nervous system stimulators and psychotomimetics.

Examples of opioid analgesics are opium and morphine contained in it, heroin semisynthesized from morphine and synthetic narcotics such as pethidine and methadone having similar pharmacological actions and dependency to them, and antagonistic analgesics such as pentazocine and buprenorphine.

Examples of central nervous system depressants are hypnotics such as barbituric acid derivatives, methaqualone, benzodiazepine derivatives and chloral hydrate; antianxiety drugs such as meprobamate and benzodiazepine derivatives; organic solvents such as thinner, alcohols and the like.

Examples of central nervous system stimulators are cocaine, which is one of typical narcotics, stimulants such as amphetamines, anorexigenic agents such as phenmetrazine, stimulators such as methylphenidate and pipradrol and drugs contained in luxury goods such as nicotine and caffeine.

Examples of psychotomimetics are hallucinogens such as LSD, DOM (2-amino-1-2,5-dimethoxy-4-methyl) phenylpropane) and mescaline, PCP (phencyclidine or "angel dust"), cannabis and the like ("NEW Pharmacology", p. 606–611, Nankodo, 1989).

The addicting drugs are also classified according to the existence of crossing of their tolerance-dependency. Morphine type addicting drugs are exemplified by morphine, codeine, methadone, pethidine and the like. Barbiturate-alcohol type addicting drugs are exemplified by barbiturates, alcohols, weak tranquilizers and the like. Cocaine type addicting drugs are exemplified by cocaine, "crack" (cocaine in ready-to-smoke form) and the like. Amphetamine type addicting drugs are exemplified by amphetamine, methamphetamine and the like. Cannabis type addicting drugs are exemplified by marijuana (THC), hashish and the like. Hallucinogen type addicting drugs are exemplified by LSD-25, mescaline, psilocibin and the like. Organic solvent type addicting drugs are exemplified by toluene, acetone, carbon tetrachloride and the like ("Opioid", p. 118–120, Kagakudojin, 1991).

It was reported that 1,4-(diphenylalkyl)piperazine derivatives, which are active ingredients of the present invention, have a strong affinity for the Σ receptor and are useful as therapeutic agents for cerebral nerve dysfunctions such as dementia, depression, schizophrenia and anxiety neurosis; diseases accompanied by immune disorders and cryptorrhea; digestive ulcer and the like (Japanese Laid-open Patent Publication No. 89949/1995). It was reported that such derivatives are useful as preventive or therapeutic agents for ophthalmopathy, particularly retinal diseases such as diabetic retinopathy and occlusion of retinal vessels and glaucoma, since such derivatives exhibit protective actions on retinal nerve cells (Japanese Laid-open Patent Publication No. 120569/1998).

Heretofore, a study of the drug dependence of the 1,4-(diphenylalkyl)piperazine derivatives was not done, and it is a very interesting subject.

SUMMARY OF THE INVENTION

Studying precisely in order to find new pharmacological actions of 1,4-(diphenylalkyl)piperazine derivatives, the present inventors found that the 1,4-(diphenylalkyl)piperazine derivatives exhibit inhibitory actions on drug dependence. Namely, the present inventors found that the 1,4-(diphenylalkyl)piperazine derivatives are useful as preventive or therapeutic agents for drug dependence due to drug abuse.

The present invention relates to a method for preventing or treating drug dependence comprising administering to a human in need thereof (such as a human having a drug dependency) a pharmaceutically effective amount of a compound represented by the following formula [I] or a salt thereof as active ingredients:

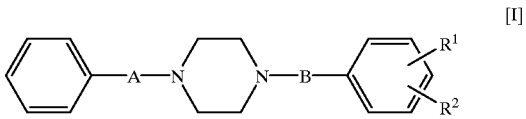

[I]

wherein $R^1$ is lower alkoxy, $R^2$ is lower alkoxy, "A" is lower alkylene and "B" is lower alkylene.

The groups defined above are described in more detail as follows. The lower alkoxy is lower alkoxy having one to six carbon atoms such as methoxy, ethoxy, propoxy or butoxy. The lower alkylene is lower alkylene having one to six carbon atoms such as methylene, ethylene, propylene or butylene.

Preferred examples of the compound are compounds wherein each group is the following in the compounds represented by the formula [I] or salts thereof:

(1a) "A" is lower alkylene having two to four carbon atoms; and/or (2a) "B" is lower alkylene having two to four carbon atoms.
Namely,
Compounds defined by above (1a) in the compounds represented by the formula [I] or salts thereof,
Compounds defined by above (2a) in the compounds represented by the formula [I] or salts thereof, and
Compounds defined by a combination of above (1a) and above (2a) in the compounds represented by the formula [I] or salts thereof.

Particularly preferred examples of the compound are compounds wherein each group is the following in the compounds represented by the general formula [I] or salts thereof;
(1b) $R^1$ is methoxy; and/or
(2b) R is methoxy.
Namely,
Compounds defined by above (1b) in the compounds represented by the formula [I] or salts thereof,
Compounds defined by above (2b) in the compounds represented by the general formula [I] or salts thereof, and
Compounds defined by a combination of above (1b) and above (2b) in the compounds represented by the general formula [I] or salts thereof.

DETAILED DESCRIPTION OF THE INVENTION

Examples of particularly preferred compounds are 1-[2-(3,4-dimethoxyphenyl)ethyl]-4-(3-phenylpropyl) piperazine represented by the following formula [II] or salts thereof.

[II]

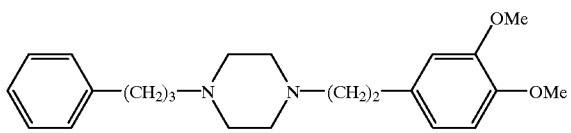

The above-mentioned salts can be pharmaceutically acceptable salts, and are exemplified by hydrochlorides, sulfates, phosphates, lactates, maleates, fumarates, oxalates and the like. The above-mentioned compounds can take the form of hydrates.

The present invention can widely be applied to the drug dependence due to drug abuse and is not limited to specific drug dependence.

As a method of calibrating the existence or the intensity of the potential of drugs to induce psychological dependence, a method has been used since olden times in which selective intake behavior or self-intake behavior toward test drugs is observed. In recent years, as a relatively simple and reliable method, a method wherein effects on conditioned place preference are indexed (CPP method) is applied ("Opioid", p. 118–120, Kagakudojin, 1991). The present inventors studied the existence or the intensity of the potential of addicting drugs to induce psychological dependence in the presence of the 1,4-(diphenylalkyl)piperazine derivatives by using this conditioned place preference test method (CPP method). Details are described in "Pharmacological Tests" hereinbelow. It is found that the 1,4-(diphenylalkyl)piperazine derivatives exhibit excellent inhibitory effects on the potential of addicting drugs to induce psychological dependence and are useful for the prevention or the treatment of drug dependence due to the abuse of addicting drugs.

Examples of dosage forms of the drugs are oral preparations such as tablets, capsules and granules, injections and the like. These preparations can be prepared by general techniques. For example, in order to prepare oral preparations such as tablets, capsules and granules, the compound [I] or salts thereof can be formulated into the preparations, if necessary, by adding an extending agent such as lactose, starch, crystalline cellulose or vegetable oil, a lubricant such as magnesium stearate or talc, a binder such as hydroxypropylcellulose or polyvinyl pyrrolidone, a disintegrator such as calcium carboxymethylcellulose, a coating agent such as hydroxypropylmethylcellulose, macrogol or a silicone resin, or a gelatin film forming agent.

The dosage is appropriately adjusted depending on symptoms, age, dosage form, type of drug dependence and the like, and in the case of the oral preparations, the usual daily dosage is 1 to 1000 mg, which can be given in a single dose or several divided doses.

BEST MODE FOR CARRYING OUT THE INVENTION

Pharmacological Tests are shown below as Examples.
Pharmacological Tests
Effects of 1,4-(diphenylalkyl)piperazine derivatives on the potency of induction of psychological dependence by addicting drugs were studied by using the conditioned place preference test (CPP method) according to the report of Suzuki et al. (Life Science, 57, 1277–1284 (1995)).

EXAMPLE 1

Effect of Test Compound on Potential of Addicting Drugs to Induce Psychological Dependence
Animals
Male Sprague-Dawley rats, body weight: about 250 g, 5.5 weeks old, were used in groups of eight.
Apparatus
An apparatus was used wherein a rectangular parallelepiped box was divided into two compartments at the center in length by a sliding partition and one compartment was made white, while the other compartment was made black.
Solutions of Test Compound and Addicting Drugs
A test compound and addicting drugs to be used were dissolved in physiological saline.
Method of Administration
The solutions of the test compound (1 mg/ml and 3 mg/ml) were administered subcutaneously to the rats (1 ml/kg). The solutions of the addicting drugs were administered subcutaneously to a morphine administration group (physiological saline and an 8 mg/ml solution of morphine hydrochloride) and intraperitonealy to a cocaine administration group (physiological saline and a 4 mg/ml solution of cocaine hydrochloride) and to a methamphetamine administration group (physiological saline and a 2 mg/ml solution of methamphetamine hydrochloride) (1 ml/kg respectively).
Place Conditioning Procedure
Pre-conditioning:
The rats were placed in the box from which the partition had been removed. Each cumulative time the rats had spent in the white compartment and the black compartment respectively was measured for 15 minutes, and the spent time in the compartment where the rats had spent a longer time (pre value) was determined from a difference between them. This operation was carried out once a day for three days.
Conditioning:
The box was divided into two compartments by the partition. The solution of the test compound was administered to the rats, and 30 minutes later, the solution of the addicting drug was further administered to the rats. The rats were confined for 50 minutes to the compartment in which the rats had spent a shorter time in pre-conditioning. The next day, only physiological saline was administered to the rats, and next the rats were confined for 50 minutes to the compartment in which the rats had spent a longer time. This training was repeated three times (2×3 days).

Post-conditioning:

The partition was removed from the box, and the conditioned rats were placed in the box. Each cumulative time the rats had spent in the white compartment and the black compartment respectively was measured for 15 minutes, and the spent time in the compartment where the rats had spent a longer time (post value) was determined from a difference between them.

Method of Measurement

The cumulative time the rats had spent in the respective compartments was measured by using an infrared sensor.

Data Analysis

The potential of the addicting drugs to induce psychological dependence was evaluated by using CPP scores (sec.) showing a motivational effect of the conditioning drug as an index.

CPP score (sec.)=post value (sec.)−pre value (sec.)

The effects of the test compound on the potential of the addicting drugs to induce psychological dependence was determined by the following equation as inhibition rates (%).

Inhibition rate (%)=[(A−B)/A]×100

A: CPP score (sec.) of physiological saline administration group

B: CPP score (sec.) of test compound administration group

Results

Experiments were carried out by using morphine hydrochloride, cocaine hydrochloride and methamphetamine hydrochloride as the addicting drugs and 1-[2-(3,4-dimethoxyphenyl)ethyl]-4-(3-phenylpropyl)piperazine dihydrochloride (hereinafter referred to as "compound A") represented by the following formula [III] as the test compound respectively. These results are shown in Table 1.

Table 1 shows that when the compound A was administered, the inhibition rates of the motivational effects of the conditioning drugs increased depending on the doses in all the administration groups, and that the compound A apparently inhibited the potential of the addicting drugs to induce psychological dependence.

EXAMPLE 2

Test of Potential to Induce Psychological Dependence of Test Compound and Addicting Drugs Animals Male Sprague-Dawley rats, body weight: about 250 g, 5.5 weeks old, were used in groups of eight.

Apparatus

An apparatus was used wherein a rectangular parallelepiped box was divided into two compartments at the center in length by a sliding partition and one compartment was made white, while the other compartment was made black.

Solutions of Test Compound and Addicting Drugs

A test compound and addicting drugs to be used were dissolved in physiological saline.

Method of Administration

The solutions of the test compound (0.3 mg/ml, 1 mg/ml and 3 mg/ml solutions) were administered subcutaneously to the rats (1 ml/kg) The solutions of the addicting drugs were administered subcutaneously to morphine administration groups (2 mg/ml, 4 mg/ml and 8 mg/ml solutions of morphine hydrochloride) and intraperitonealy to cocaine administration groups (2 mg/ml, 4 mg/ml and 8 mg/ml solutions of cocaine hydrochloride) and to methamphetamine administration groups (1 mg/ml, 2 mg/ml and 4 mg/ml) (1 ml/kg respectively). Physiological saline was administered by the same method as the method of administration of each administration group (1 ml/kg respectively).

Place Conditioning Procedure and Measurement

Pre-conditioning:

The rats were placed in the box from which the partition had been removed. Each cumulative time the rats had spent in the white compartment and the black compartment respectively was measured for 15 minutes, and the spent time in the compartment where the rats had spent a longer time (pre-value) was determined from a difference between them. This operation was carried out once a day for three days.

TABLE 1

[III]

⟨phenyl⟩—(CH$_2$)$_3$—N⟨piperazine⟩N—(CH$_2$)$_2$—⟨phenyl with OMe, OMe⟩ · 2HCl

| Addicting drug | Inhibition rate (%)* | |
|---|---|---|
| | Compound A (1 mg/kg) | Compound A (3 mg/kg) |
| Morphine administration group | 38 | 50 |
| Cocaine administration group | 26 | 55 |
| Methamphetamine administration group | 55 | 57 |

*Average of eight samples in one group

Conditioning:

The box was divided into two compartments by the partition. The solution of the addicting drug or the solution of the test compound was administered subcutaneously to the rats. The rats were confined for 50 minutes to the compartment in which the rats had spent a shorter time in pre-conditioning. The next day, physiological saline was administered subcutaneously to the rats and, next, the rats were confined for 50 minutes to the compartment in which the rats had spent a longer time. This training was repeated three times (2×3 days).

Post-conditioning:

The partition was removed from the box, and the conditioned rats were placed in the box. Each cumulative time the rats spent in the white compartment and the black compartment respectively was measured for 15 minutes, and the spent time in the compartment where the rats had spent a longer time (post value) was determined from a difference between them.

Method of Measurement

The cumulative time the rats had spent in the respective compartments was measured by using an infrared sensor.

Data Analysis

The potential to induce psychological dependence was evaluated by using CPP scores (sec.) showing a motivational effect of the conditioning drug as an index.

The motivational effects of the addicting drugs and the test compound, which were the conditioning drugs, were determined by the following equation.

CPP score (sec.)=post value (sec.)−pre value (sec.)

Results

Table 2 shows test results using morphine hydrochloride and cocaine hydrochloride. Table 3 shows test results using methamphetamine hydrochloride. Table 4 shows test results using the compound A as the test compound.

TABLE 2

|  | CPP score (sec.)* | | | |
| --- | --- | --- | --- | --- |
|  | Physiological saline | 2 mg/kg | 4 mg/kg | 8 mg/kg |
| Morphine administration group | 19 | 171 | 187 | 228 |
| Cocaine administration group | 19 | 141 | 178 | 259 |

*Average of eight samples in one group

TABLE 3

|  | CPP score (sec.)* | | | |
| --- | --- | --- | --- | --- |
|  | Physiological saline | 1 mg/kg | 2 mg/kg | 4 mg/kg |
| Methamphetamine administration group | 19 | 155 | 224 | 151 |

*Average of eight samples in one group

Tables 2 and 3 show that when morphine, cocaine or methamphetamine, which is the addicting drug, is administered, the motivational effects (CPP score (sec.)) of the conditioning drugs are plus and these addicting drugs have appetitive effects (potential to induce psychological dependence).

TABLE 4

|  | CPP score (sec.)* | | | |
| --- | --- | --- | --- | --- |
|  | Physiological saline | 0.3 mg/kg | 1 mg/kg | 3 mg/kg |
| Compound A administration group | −13 | −37 | −45 | −64 |

*Average of eight samples in one group

On the other hand, Table 4 shows that when the compound A is administered, the conditioning drug exhibits no motivational effect (CPP score (sec.)) at any doses and the compound A has no potential to induce psychological dependence.

From the above-mentioned results, it is recognized that the 1,4-(diphenylalkyl)piperazine derivatives exhibit inhibitory effects on the potential of addicting drugs to induce psychological dependence and are useful as preventive or therapeutic agents for drug dependence due to drug abuse.

Industrial Applicability

The present invention provides drugs which contain 1,4-(diphenylalkyl)piperazine derivatives as active ingredients and are useful for the prevention or treatment of drug dependence due to drug abuse.

What is claimed is:

1. A method for the prevention or treatment of a drug dependence comprising administering to a human in need thereof a 1,4-(diphenylalkyl)piperazine compound represented by the following formula [I] or a pharmaceutically acceptable salt thereof,

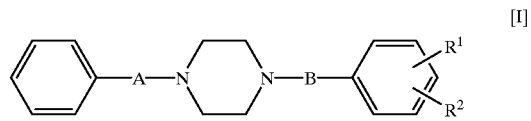

wherein $R^1$ is lower alkoxy, $R^2$ is lower alkoxy, A is lower alkylene and B is lower alkylene.

2. The method of claim 1, wherein the compound has the following formula [II]:

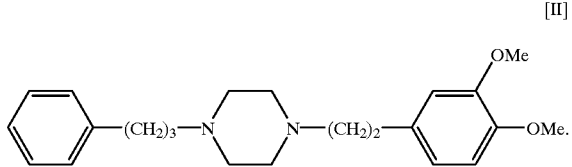

3. The method of claim 1, wherein the drug dependence is selected from the group consisting of a morphine-induced drug dependence, a cocaine-induced drug dependence, a methamphetamine-induced drug dependence, a nicotine-induced drug dependence, an alcohol-induced drug dependence, a phencyclidine-induced drug dependence and a benzodiazepine derivative-induced drug dependence.

4. The method of claim 2, wherein the drug dependence is selected from the group consisting of a morphine-induced drug dependence, a cocaine-induced drug dependence, a methamphetamine-induced drug dependence, a nicotine-induced drug dependence, an alcohol-induced drug dependence, a phencyclidine-induced drug dependence and a benzodiazepine derivative-induced drug dependence.

5. The method of claim 1, wherein the method is for treatment of a drug dependence.

6. The method of claim 1, wherein the method is for prevention of a drug dependence.

7. The method of claim 1, wherein the 1,4-(diphenylalkyl) piperazine compound is administered in a daily dose of 1 to 1000 mg.

8. The method of claim 7, wherein the daily dose is administered in a single dose.

9. The method of claim 7, wherein the daily dose is administered in more than one divided doses.

* * * * *